(12) United States Patent
Dimitrova et al.

(10) Patent No.: US 10,528,758 B2
(45) Date of Patent: Jan. 7, 2020

(54) GENOMIC INFORMATICS SERVICE

(71) Applicants: KONINKLIJKE PHILIPS N.V., Eindhoven (NL); INTERTRUST TECHNOLOGIES CORPORATION, Santa Clara, CA (US)

(72) Inventors: Nevenka Dimitrova, Eindhoven (NL); William Knox Carey, Mountain View, CA (US); Raymond J. Krasinski, Suffern, NY (US); Jarl Nilsson, Mountain View, CA (US); Bart Grantham, San Francisco, CA (US); Alexander Ryan Mankovich, Eindhoven (NL); Vartika Agrawal, Eindhoven (NL)

(73) Assignees: Koninklijke Philips N.V., Eindhoven (NL); Intertrust Technologies Corporation, Sunnyvale, CA (US)

( * ) Notice: Subject to any disclaimer, the term of this patent is extended or adjusted under 35 U.S.C. 154(b) by 0 days.

(21) Appl. No.: 15/307,843

(22) PCT Filed: Apr. 24, 2015

(86) PCT No.: PCT/IB2015/053003
§ 371 (c)(1),
(2) Date: Oct. 31, 2016

(87) PCT Pub. No.: WO2015/166389
PCT Pub. Date: Nov. 5, 2015

(65) Prior Publication Data
US 2017/0068826 A1    Mar. 9, 2017

Related U.S. Application Data

(60) Provisional application No. 62/024,012, filed on Jul. 14, 2014, provisional application No. 61/987,887, filed on May 2, 2014.

(51) Int. Cl.
G06F 21/62 (2013.01)
G06F 21/32 (2013.01)
(Continued)

(52) U.S. Cl.
CPC .......... *G06F 21/6245* (2013.01); *G06F 21/32* (2013.01); *G16B 50/00* (2019.02); *G16H 10/60* (2018.01)

(58) Field of Classification Search
CPC ...... G06F 21/6245; G06F 21/32; G06F 19/28; G16H 10/60
See application file for complete search history.

(56) References Cited

U.S. PATENT DOCUMENTS 5,974,549 A * 10/1999 Golan .................. G06F 9/468
714/47.3
7,309,001 B2  12/2007 Banfield et al.
(Continued)

OTHER PUBLICATIONS

William Stallings, "Computer Organization and Architecture Designing for Performance: Eighth Edition", 2010, Prentice Hall, pp. 1-881.*

(Continued)

*Primary Examiner* — Robert B Leung
*Assistant Examiner* — Thomas Ho

(57) ABSTRACT

Methods and apparatus for a secure framework for storing and analyzing genomic data. Embodiments of the present invention apply persistent governance to sensitive information and to the analytics that operate upon it, managing the interaction between the two.

20 Claims, 5 Drawing Sheets

(51) Int. Cl.
*G16H 10/60* (2018.01)
*G16B 50/00* (2019.01)

(56) References Cited

U.S. PATENT DOCUMENTS

| | | | |
|---|---|---|---|
| 9,270,446 B2 | 2/2016 | Ayday et al. | |
| 2002/0029156 A1* | 3/2002 | O'Dowd | G16H 10/40 705/3 |
| 2002/0128860 A1* | 9/2002 | Leveque | G06F 19/324 705/2 |
| 2004/0073460 A1 | 4/2004 | Erwin | |
| 2006/0004588 A1 | 1/2006 | Ananda | |
| 2009/0228304 A1 | 9/2009 | Ciarniello et al. | |
| 2010/0027780 A1* | 2/2010 | Jung | G06Q 10/10 380/28 |
| 2010/0034376 A1* | 2/2010 | Okuizumi | G06F 21/6254 380/44 |
| 2013/0096943 A1* | 4/2013 | Carey | G06Q 10/10 705/2 |
| 2013/0246460 A1* | 9/2013 | Maltbie | G06F 19/18 707/771 |
| 2014/0075183 A1 | 3/2014 | Wang et al. | |
| 2014/0282889 A1* | 9/2014 | Ishaya | H04L 63/08 726/4 |
| 2016/0048564 A1* | 2/2016 | Bassett, Jr. | G06F 19/30 715/230 |
| 2017/0308717 A1* | 10/2017 | Huang | G06F 19/28 |

OTHER PUBLICATIONS

"Principles of Operation", 1953, IBM computers, pp. 1-94.*
Bottomley et al. "Containers", p. 1-5, ;login Magazine: Oct. 2014, vol. 39, No. 5.*
W Knox Carey et al: "Securing Genomic Computations for Research and Clinical Decision Support", Jun. 30, 2014 (Jun. 30, 2014), XP055199799,Retrieved from the Internet: URL:http://seclab.soic.indiana.edu/GenomePri vacy/papers/Genome Pri vacy-paperl3.pdf.
Jyotiprakash Sahoo et al:"Virtualization: A Survey on Concepts,Taxonomy and Associated Security Issues", Computer and Network Technology (ICCNT),2010 Second International Conference on, IEEE, Piscataway, NJ, USA, Apr. 23, 2010 (Apr. 23, 2010), pp. 222-226.

* cited by examiner

GENOMIC INFORMATICS SERVICE

CROSS-REFERENCE TO RELATED APPLICATIONS

The present application claims the benefit of U.S. provisional application No. 62/024,012, filed on Jul. 14, 2014, and U.S. provisional application No. 61/987,887, filed on May 2, 2014. The entire disclosure of these applications is hereby incorporated by reference as if set forth in its entirety herein.

FIELD

The present invention generally relates to the delivery of genomic information, and more specifically to the secure delivery of genomic information using a hosted service.

BACKGROUND

With each generation of genomic sequencing systems, an unprecedented amount of molecular information becomes available for clinical diagnosis and treatment planning. This is particularly the case in oncology, where high-throughput molecular profiling is the key driver towards personalization of diagnostics, therapy selection and response assessment. As such, decision support systems for generating and providing informatics using sequence data of patient DNA can be critically important tools.

When genomic information is used to make clinical decisions, it is typically used in a linear fashion, where a set of standard analysis steps are sequentially performed to transform the raw genomic sequence to yield a particular set of informatics products, e.g. biomarkers, genetic variants, or other patient-specific features. This set of genomic information is then processed specifically for one patient within a single study, or for the purpose of answering one clinical question. Thus, conventional genomic informatics are generated without providing an opportunity to explore multiple clinical options, or to assess patient-specific data in the context of population-based cohorts including other patients' genomic information.

One of the largely unmet requirements for conventional genomic informatics systems is the need to provide genomic information security and privacy. Genomic or any information that can be used to identify patients is subject to government and industry regulation. Institutions and individuals that hold patient-identifying information, including those in research and clinical settings, are further required to notify patients in the event that data security or privacy is breached. As a result, genomic data holders are reluctant to share patient-specific genomic information.

Conventional systems and methods are limited in their capacity to protect genomic information with sufficient granularity and contextual sophistication. For example, as shown in FIG. 1, conventional data releases that include patient-specific genomic information focus on the proper credentialing of researchers, clinicians, and their affiliated institutions. Once the individual or institution is granted access, the genomic information in its raw form and the responsibility of protecting the information is passed onto the recipient. This approach, by far the most common, has several serious drawbacks from a security point of view. For example, it assumes that security can be maintained in subsequent distribution or dissemination of the information through transitive trust relationships when, in fact, subsequent recipients of the information can cause inadvertent privacy breaches.

This approach also does not provide any detailed audit information on individual instances of information access, despite its limitation that all of the data for a large study be centralized. In this approach, the security or privacy policies governing the use of the information cannot change dynamically or are simply not enforced, and often the recipients must be trusted to enforce the policies themselves.

Another conventional method provides an application programming interface (API) for providing secure access to the information via trusted data stores. This approach has two significant advantages. If the recipients are required to authenticate themselves, it is possible to discriminate amongst different recipients and apply potentially different policies to their accesses. This method can provide fine-grained access; recipients can ask only for the data required for a particular task. The information disclosed, or potentially disclosed, can be metered and audited. This level of auditing also allows potential sources of the leaks to be identified.

On the other hand, this approach still returns sensitive data into an untrusted environment. To see where this might pose a problem, consider a simple example: given a list of genome identifiers, determine the number of genomes that have a particular variant. Suppose that the API simply returns variants by identifier. Under these circumstances, the untrusted code will learn the individual variants for each of the genomes in the list, which were presumably chosen based on phenotypical characteristics. Those associations may be compromised, thereby weakening security.

SUMMARY

This summary is provided to introduce a selection of concepts in a simplified form that are further described below in the Detailed Description section. This summary is not intended to identify or exclude key features or essential features of the claimed subject matter, nor is it intended to be used as an aid in determining the scope of the claimed subject matter.

Embodiments of the present invention relate to methods and apparatus for a secure framework for storing and analyzing genomic data. Embodiments of the present invention apply persistent governance to sensitive information and to the analytics that operate upon it, managing the interaction between the two.

In one aspect, embodiments of the present invention relate to a method of securing genomic information. The method includes receiving a genomic sequence from a source of genomic data, generating a proxy patient identify for referencing the genomic sequence; providing the genomic sequence to a managed computing pipeline, obtaining the detected feature from the managed computing pipeline; and annotating the detected feature using a hosted computing module. The computing pipeline is configured to process the genomic sequence so as to detect a feature in the genomic sequence.

In one embodiment, the genomic sequence is received from a sequencing apparatus. In one embodiment, the method further includes storing at least one of the detected feature, the annotated feature, and the proxy identity in a database according to an auditable sequence of execution of the hosted computing module. In one embodiment, the hosted computing module is configured to annotate the detected feature according to a clinical reference. In one embodiment, the method further includes aligning the genomic sequence against a reference genomic sequence prior to providing the genomic sequence to the managed computing pipeline.

In one embodiment, the step of providing the hosted computing module includes providing a hosted computing module having a program execution module comprising a virtualization container and a security module for authenticating users and providing access control according to the user authentication. In one embodiment, the step of providing the genomic sequence to the managed computing pipeline includes providing a managed computing pipeline secured by one of user authentication and role-based access control. In one embodiment, the method further includes presenting at least one annotated feature and the associated patient proxy identity for clinical analysis.

In another aspect, embodiments of the present invention relate to an apparatus for providing genomic information. The apparatus includes a receiver module, an identity generator, a communication bus, and a hosted computing module. The receiver module is configured to receive a genomic sequence from a source of genomic data. The identity generator is configured to generate a proxy patient identity for referencing the genomic sequence. The communication bus provides the genomic sequence to a managed computing pipeline, the computing pipeline being configured to process the genomic sequence so as to detect a feature in the genomic sequence. The communication bus is further configured to obtain the detected feature from the managed computing pipeline, and to provide the detected features to a hosted computing module. The hosted computing module is configured to annotate the detected feature.

In one embodiment, the source of genomic data is a sequencing apparatus. In one embodiment, the apparatus further includes a non-transitory computer readable storage medium for storing at least one of the detected feature, the annotated feature, and the proxy identity in a database according to an auditable sequence of execution of the hosted computing module. In one embodiment, the hosted computing module is configured to annotate the detected feature according to a clinical reference.

In one embodiment, the apparatus further includes a module configured to align the genomic sequence against a reference genomic sequence prior to providing the genomic sequence to the managed computing pipeline. In one embodiment, the hosted computing module includes a program execution module comprising a virtualization container and a security module for authenticating users and providing access control according to the user authentication. In one embodiment, the managed computing pipeline is secured by one of user authentication and role-based access control. In one embodiment, the apparatus further includes a user interface for presenting at least one annotated feature and the associated patient proxy identity for clinical analysis.

In yet another aspect, embodiments of the present invention relate to a method for performing a computation. The method includes receiving a program for execution at a managed computing pipeline, creating an execution context for the execution of the program, launching a virtual machine within the execution context to execute the program; and transmitting the results of execution out of the managed computing pipeline, wherein personally-identifiable information associated with the execution of the program is stored exclusively within the execution context.

In one embodiment, the method further includes creating an executable image from the uploaded program and saving the executable image to a non-transitory computer readable storage medium. State information associated with the execution of the virtual machine may also be stored in the non-transitory computer readable storage medium. In one embodiment, the execution context is a virtualization container.

These and other features and advantages, which characterize the present non-limiting embodiments, will be apparent from a reading of the following detailed description and a review of the associated drawings. It is to be understood that both the foregoing general description and the following detailed description are explanatory only and are not restrictive of the non-limiting embodiments as claimed.

BRIEF DESCRIPTION OF DRAWINGS

Non-limiting and non-exhaustive embodiments are described with reference to the following figures in which.

In the drawings, like reference characters generally refer to corresponding parts throughout the different views. The drawings are not necessarily to scale, emphasis instead being placed on the principles and concepts of operation.

DETAILED DESCRIPTION

Figure 1:
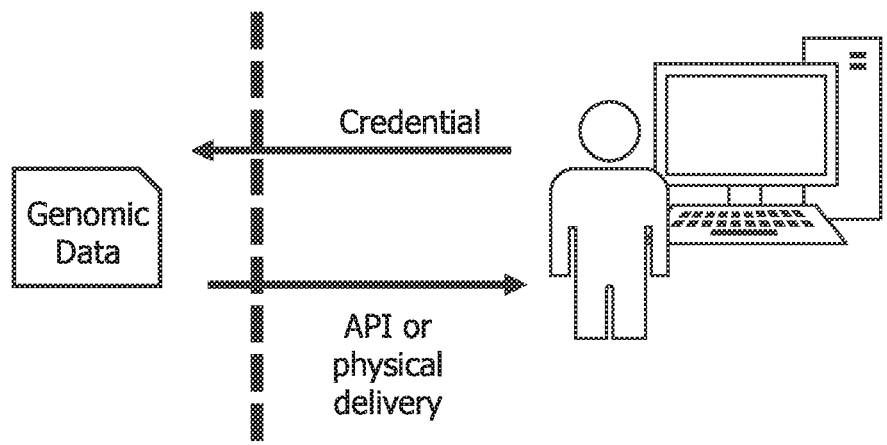
FIG. 1 is a block diagram of a conventional system for access to genomic information.

Various embodiments are described more fully below with reference to the accompanying drawings, which form a part hereof, and which show specific exemplary embodiments. However, embodiments may be implemented in many different forms and should not be construed as limited to the embodiments set forth herein; rather, these embodiments are provided so that this disclosure will be thorough and complete, and will fully convey the scope of the embodiments to those skilled in the art. Embodiments may be practiced as methods, systems or devices. Accordingly, embodiments may take the form of a hardware implementation, an entirely software implementation or an implementation combining software and hardware aspects. The following detailed description is, therefore, not to be taken in a limiting sense.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the description that follow are presented in terms of symbolic representations of operations on non-transient signals stored within a computer memory. These descriptions and representations are the means used by those skilled in the data processing arts to most effectively convey the substance of their work to others skilled in the art. Such operations typically require physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions that could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The processes and displays presented herein are not inherently related to any particular computer or other apparatus. Various general purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the claims.

Figure 2:
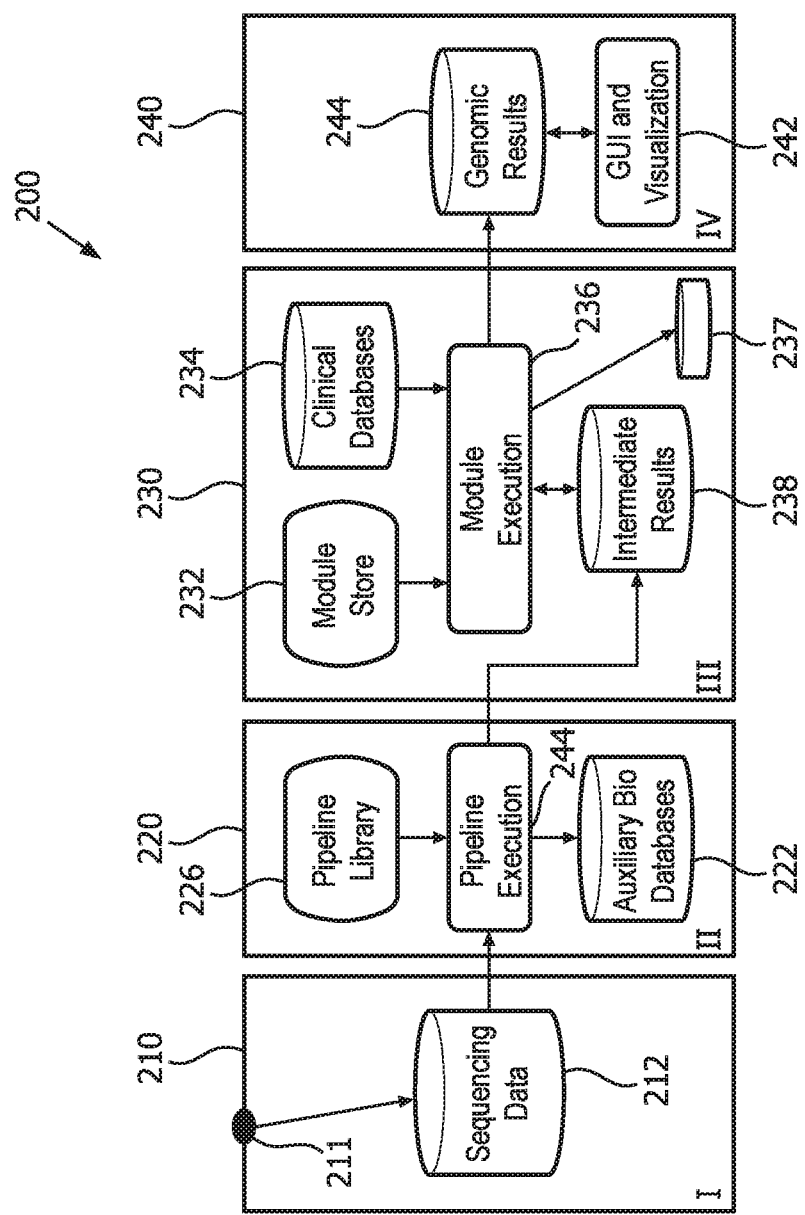
FIG. 2 is a block diagram of a multiple stage computing system for generating informatics in accord with the present invention.

According to one embodiment, as shown in FIG. 2, there is provided a multiple stage computing system 200 for generating informatics for research or clinical studies of genomic sequences. The computing system includes four stages, 210, 220, 230, and 240, each of which can be provided with one or more security and privacy preservation measures (hereinafter, referred as Protection Measures).

In stage I (210), raw sequences of genomic data can be received from a genomic sequencer (not shown), and the received genomic sequences can be stored in database 212. The set of raw, unaligned genomic sequence reads can be produced at a sequencing machine and transported into the system. Since the reads are not yet aligned, i.e., and are effectively in a random order, the reads are equivalent from a security point of view. The appropriate Protection Measures are, accordingly, directed to the protection of the raw read data and secure transmission to the server.

According to one embodiment of the present invention, the Protection Measures can include encryption of the reads. For example, the encryption of the reads can be performed with a symmetric key. The Protection Measures can further include encryption of the symmetric key with a public key of the computer at which the reads are received and ingested for subsequent processing. Once encrypted, the reads data can be uploaded to the ingestion point 211, decrypted and stored in database 212.

Next, in stage II (220), a computing pipeline module can be provided to further process the raw genomic sequences received in stage I (210), transforming them into a set of annotated variants. Here, the pipeline module can be provided by one or more computer processors executing a series of data processing instructions, thereby forming a series of pipeline processors. The output of one pipeline processor is the input to the next one. The instruction sets of the pipeline module can be executed in parallel or in a time-division multiplexed manner. In other words, the pipeline processors can be arranged as multiple parallel pipelines.

Figure 3:
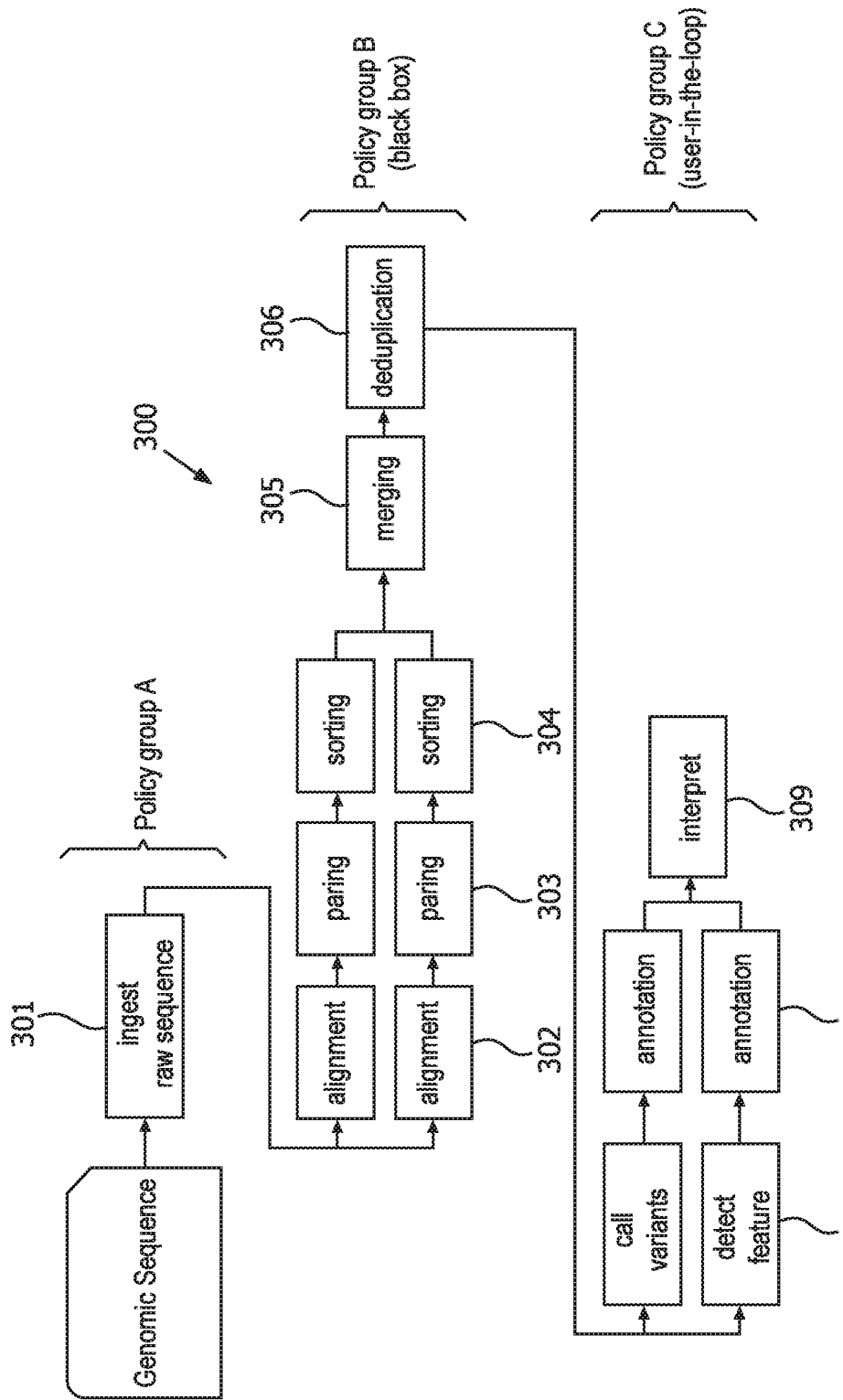
FIG. 3 depicts an example of the processing of genomic sequence data using an embodiment of the present invention.

As shown in FIG. 3 and in conjunction with FIG. 2, in this stage, the raw reads can be aligned to a reference genomic sequence with one set of instructions 302. The output of pipeline processor 302 can be provided to pipeline processor 303, which can pair the aligned read sequences. Subsequent pipeline processor 304 can sort the paired sequences, for example, against a reference genomic sequence. The sorted sequences can be merged into a single sequence by pipeline processor 305 and deduplication of sequences can be performed by pipeline processor 306.

The output of the pipeline processor can organize the genomic sequences in a way that reveals more patient information, and can be more useful to an attacker. However, data volume can remain large at this stage, and so it can be less sensitive to small quantity data breaches.

Furthermore, in stage II (220 in FIG. 2), since the alignment instruction set can involve all of the reads, each alignment process (performed by a pipeline processor) can be granted equal access to all reads without slowing it down with encryption operations. In other words, the Protection Measures applied to the pipeline processors, according to one embodiment of the present invention, includes conventional security techniques such as authentication of users, role-based access control, security audits, and the like.

According to one embodiment, if the pipeline processors can process the genomic sequences without user interaction, i.e. automatic execution of the data processing instruction sets, authentication and authorization of the user can be omitted from the Protection Measures.

According to another embodiment, pipeline processors 308 and 309 can require user interaction or input. For example, pipeline processor 308 annotates a genomic feature, i.e. a variant output from the previous pipeline processor 307. The genomic feature can be annotated with annotation retrieved from any of a plurality of annotation databases (shown as Auxiliary Bio Databases 222 in FIG. 2), such as dbSNP, COSMIC, ClinVar and dbNSFP The selection of one of such databases can be defaulted, i.e. without user input, or the selection can be offered to the user and made according to user input based on the kind of information and the level of detail desired.

As another example, pipeline processor 309 can assist a user to interpret the genomic features annotated by the pipeline processor 308. Based on the genomic features identified as well as the information from published literature or available medical knowledge presented, the clinician can interpret the clinical relevance of the genomic features and annotations, in order to decide the course of treatment for a patient. As a result, treatment can be personalized for the patient based on the patient's genomic, transcriptomic and clinical profile.

According to one embodiment, a final output of this stage, stage II (220 in FIG. 2) can be an annotated set of variants, which can be extremely private and may be subject to different security policies depending upon the relative sensitivity of the variants. When running operations against this data, embodiments of the present invention will track the requester of the operation, the purpose of the request, and whether the user has been authorized to make this request. In some embodiments, as discussed in further detail below, the software performing the operations may be run in a secure environment so that their access to the sensitive data may be controlled more carefully and the ability to perform illegitimate accesses may be hindered.

According to one embodiment, variants related to phenotypes such as diseases can require more stringent access policies as a part of the Protection Measures of the present invention.

According to another embodiment of the present invention, a proxy identity can be generated for referencing the genomic sequence for features output by each of the pipeline processors. As such, each of the pipeline processors can be operated without patient-identifying information.

Next, in stage III (230 in FIG. 2), a hosted computing module 238 is provided to receive the genomic features and sequence information (Intermediate Results) output from stage II (223), and the Intermediate Results can be stored in a database 238. According to one embodiment, the hosted computing module permits third party program code to be executed over the received Intermediate Result, in order to further generate informatics products, under the Protection Measures according to the present invention. Third party program code can include user-selected or user-created program codes, either in source code or binary forms.

In previous stages, computations are performed without necessarily revealing the results of these computations to users; the results of the computations may be stored in a database for later access. In this phase, on the other hand, sensitive information may be revealed to an end user, which requires that the user be authenticated, and any policies governing the user's access to the output of a given module be checked.

The genomic API model described above, according to various embodiments of the present invention, addresses many of the deficiencies of the conventional direct access model, especially when computations that can reveal information as a side effect are performed behind an API, out of reach of untrusted client-side code. Yet it is difficult to design an API that obscures all such computations, and thus it is inevitable that untrusted code will have access to some intermediate products, revealing more information than is strictly necessary.

Various embodiments of the present invention address this issue by offering general-purpose computational capability within a trusted boundary. Moving computations into a trusted environment allows for much more precise control over the information disclosed, as only the information revealed by the final result is visible to untrusted code. Intermediate results remain within the trusted boundary. However, allowing arbitrary code to execute within a trusted environment changes the threat model—malicious or incorrect code might compromise sensitive data, revealing it in unanticipated ways.

Further embodiments of the invention utilize a variety of techniques, either singularly or in combination, to mitigate these threats. Some embodiments require foreign code to be signed by competent authorities, and the signature checked as a condition for code loading or execution. Some embodiments track the information accessed by executing foreign code. Some embodiments execute foreign code in a sandboxed environment that prevents the foreign code from accessing arbitrary storage or network locations and allows the system to limit exposure to sensitive data. Some embodiments offer a fine-grained API for foreign code to access data, improving auditability and minimizing the amount of personal information that might be compromised by a given computation.

A program written for execution against an embodiment of the present invention may be developed in a secure or unsecure environment using, e.g., REST APIs, for data access. Each server hosting sensitive data will typically offer its own semantically-appropriate API. Programs may be tested using, e.g., publicly-available data over unsecured HTTP connections to ensure that they work properly.

Figure 4:
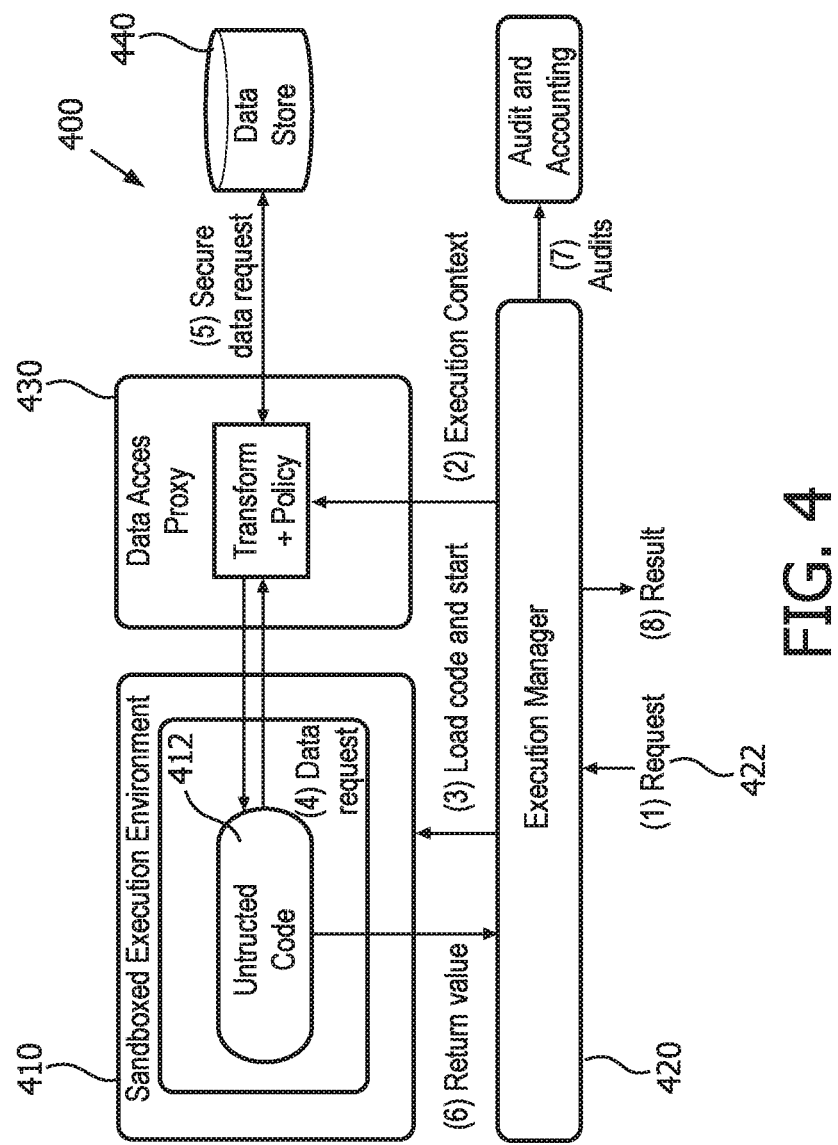
FIG. 4 illustrates an example of a hosted computing module in accord with the present invention.

According to one embodiment, as shown in FIG. 4, the hosted computing module 400 can include a sandboxed, or hosted execution environment 410. The hosted execution environment 410 can be provided in a computer virtualization system, for example, using the Linux containers mechanism (lxc). When user-created programs are loaded into the virtualization container, an executable image of the virtualized computing resources is created and stored in an image repository (not shown). At execution time, the executable image can be retrieved from the repository.

As shown in FIG. 4, in step (1), a request 422 to execute a user-created, untrusted program 412 is received by an Execution Manager 420. Although not shown in the figure, the request 422 is assumed to have first passed through authentication and authorization stages ensuring that the user requesting the execution is allowed by policy to do so. In response to an authenticated and authorized request 422, the Execution Manager 420 directs the hosted execution environment 410 to load the user-created code and to further check against a user-specific execution policy that can places conditions on the code itself, such as requiring a digital signature from a relevant authority.

In step (2), the Execution Manager 420 creates an execution context for an instance of execution of the program 412. The execution context can allow the hosted execution module 400 to associate sensitive information with the execution instance without placing that information into the memory address space of the untrusted program 412, where it can be vulnerable. For example, the program can be passed an ephemeral genome ID as its first argument, and the execution context stores its mapping to a real identifier.

The program execution can begin in step (3), with the Execution Manager 420 starting the virtual machine instance and passing in the necessary parameters. As the program 412 executes, it is permitted to request data from a data store 440 over an HTTP API, as shown in step (4). Because the program is running inside a hosted container, its access to network resources can be restricted to only trusted endpoints. Before these calls reach the data store 440, several processes can be provided:

1. The request is potentially transformed using information stored in the execution context. For example, in this step, the system might determine how the ephemeral identifiers given to a program as parameters map to actual identifiers in a data store. Information about the execution context may also be passed along to the data store as part of the request.

2. The request, which can be made over plain HTTP, is promoted to HTTPS, with certificates at both the client and server. This ensures that only certified systems can interact with trusted data stores 440, and keeps keying information out of the address space of the third-party program. Policies are applied to authorize the request. These policies offer more granular control over access to sensitive data because they can be applied as a computation proceeds, rather than before it begins. In general, the set of requests a program will make cannot be determined in advance.

3. The destination of the request may be rewritten. For example, if a request can be satisfied by a number of different servers, the proxy can direct the request to the most appropriate server.

4. The request can be logged and provided for audit at a later time.

The results of the request, after being transformed again with information in the execution context, are returned into the address space of the untrusted code 412. When the program terminates, its output can be captured by the Execution Manager 420 (step 6), audited (step 7), and returned back to the original requester (step 8).

According to one embodiment, audits are digitally signed so that they can be verified later. Because the hosted computing module 400 depends on virtualization on known virtual machines, and because the module 400 stores, signs, and tags all state information, it is possible to completely recreate a computation at a later time or a different location to validate these audits.

Figure 5:
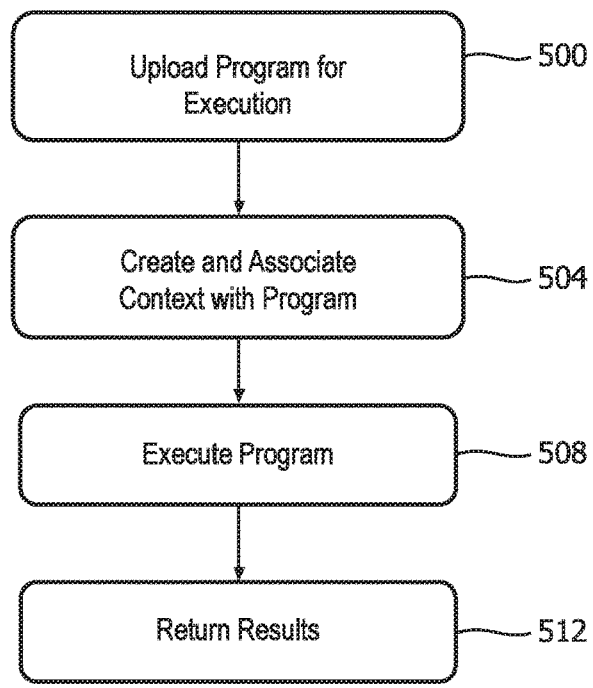
FIG. 5 is a flowchart of a method for performing a computation according to the present invention.

As shown in FIG. 5, embodiments of the present invention offer a method for performing a computation. Once a program is developed and tested, it may be uploaded for execution in a governed environment (Step 500). The developer is typically certified (i.e., authenticated) prior to uploading, and the upload process may include options that permit the uploader to set policies and conditions governing the execution of the uploaded program.

Once uploaded, executable images may be created from the uploaded programs and saved to a repository for retrieval at execution time. In order to provide isolation and security, the executed images are executed in virtualization containers such as, e.g., Docker (http://docker.io), a virtualization system based on the Linux containers mechanism (lxc).

When an embodiment receives a request to execute a program, an execution context is created for use with that particular instance of the executing program (Step 504). The execution context allows the inventive system to associate sensitive information with the running instance without placing that information into the address space of the untrusted program, where it might be vulnerable. For example, the program may be passed an ephemeral genome ID as its first argument, and the execution context stores the mapping of the genome ID to a real identifier.

The program is executed (Step 508), launching a virtual machine instance and passing in the necessary parameters. As the program executes, it may request data from a data store using, e.g., an HTTP API. Because the program is running inside a container, its access to network resources can be restricted to only trusted endpoints. Before these calls reach the data store, however, several additional steps may occur:

The request may be transformed using information stored in the execution context. For example, the system might determine how the ephemeral identifiers given to a program as parameters map to actual identifiers in a data store. Information about the execution context may also be passed along to the data store as part of the request.

The request, if originating over plain HTTP, may be promoted to HTTPS, with certificates at both the client and server. This ensures that only certified systems can interact with trusted data stores, and keeps keying information out of the address space of the third-party program.

Policies are applied to authorize the request. These policies offer more granular control over access to sensitive data because they are applied as a computation proceeds, rather than before it begins.

The destination of the request may be rewritten. For example, if a request can be satisfied by a number of different servers, the proxy may direct the request to the most appropriate server, e.g., the server that requires the least transfer of information.

The request is logged.

The results of the request—possibly after being transformed again with information in the execution context—are returned into the address space of the untrusted code (Step 512). When the program terminates, its output may be captured, audited, and returned to the original requester. Audits may be digitally signed so that they may be verified later.

Because the execution system uses virtualization on known virtual machines, and because the system stores, signs, and tags all state information, it is possible to recreate a computation at a later time and/or a different location to validate these audits.

In this model, potentially information-revealing computations are sandboxed, limiting access to intermediate products. More complex computations, however, may consist of multiple stages that can be further isolated in order to improve security and reduce information leakage.

Figure 6:
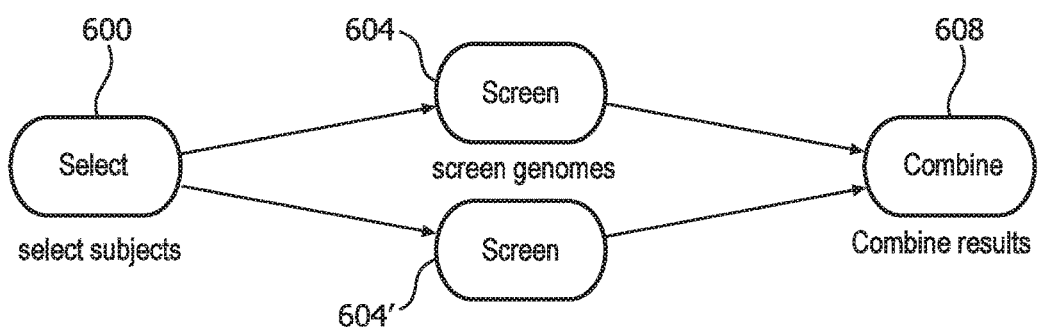
FIG. 6 is a depiction of a simple computational network for carrier compatibility detection implemented using an embodiment of the present invention.

For example, consider a simple computation that evaluates the genetic disease carrier compatibility of two subjects. It is possible to create a single program that looks up two subjects by a phenotypic identifier, checks for the presence or absence of a variant, and determines whether both subjects are carriers. In the worst case, this single program could leak personally-identifiable information However, as illustrated in FIG. 6, it is possible to transform this program into a network of three separate programs that may be executed using an embodiment of the present invention such that each program, run in isolation, cannot make the connection between genotype and phenotype. In FIG. 6, each of the three different computations has been separated into an isolated address space and joined into a computational network.

The Select computation 600 chooses two subjects, presumably based on phenotypical criteria. Each of these identifiers is mapped by the system into a genome identifier outside of the address space of either of the programs.

Each genome is then assessed separately in a Screen process 604, 604', which checks for the presence of a particular variant and passes a boolean value on to the Combine process 608, which performs a logical AND to determine carrier compatibility.

As is evident, although the computation performed by this network is the same as that computed by a single program, the amount of personally-identifiable information that might possibly be released is greatly reduced.

Embodiments of the present invention may include a mechanism for a user to specify computational networks such as the one shown in FIG. 6. Once the network is specified, the system takes care of the necessary transformations between modules, lifecycle management, storage and transport of intermediate products, and returning the final result.

This same technique may also be utilized by one of ordinary skill to convert other programs for execution on a system embodying the present invention, decomposing the programs into their individual computations each having their own isolated address spaces.

In some circumstances, the genomic API model may provide sufficient protection. When developing a framework using an object-relational model (ORM), modules can be adapted in a natural way to interact with a secure API. An ORM allows developers using web services frameworks such as Ruby on Rails or Django to interact with automatically-generated model objects whose class corresponds to a database table, and whose object instances correspond to rows within that table. Many web frameworks allow developers to interact transparently with a model object stored in a remote server over a REST API in precisely the same manner as for a local object.

As an example of the Object/REST mapping, it is possible to translate a statement that would normally retrieve a database record like patient.rsid(1933437) into a URL, where the genome ID is associated with the patient object in the local database and the path is constructed automatically by the Object/REST mapping layer. The request may also be coupled with an authentication mechanism that allows the code making the request to be identified and audited.

Integration at the API level is appropriate when modules:
Come from a trusted source that does not need to be authenticated during the transactions;
Have been analyzed for undesired behavior;
Do not require proof of integrity for access to the sensitive data;
Are executed in a trusted environment that can ensure that the sensitive information being retrieved by the modules cannot be compromised by other components;
Can pass intermediate products between one another safely.

In cases where one or more of these conditions do not hold, some protection may be afforded by applying the sandboxing technique described above at the individual module level. Approaches for implementing this type of module-level sandboxing include:
Sandboxed modules may be invoked by controller code directly. If desired, the modules themselves can use the Object/REST mapping as described above, with the adapter being injected as a dependency into the virtualization container. This approach may work well in cases where there are not many dependencies on other model objects, or where the necessary parameters can be passed to the sandboxed modules as parameters.
By adding a level of indirection; rather than mapping instance variables and method accesses to REST calls that return those items, an object mapping can convert those requests into commands to execute the sandboxed models, passing in the necessary parameters.

Using this integration strategy, the system can safely handle third-party code, cryptographically verify code integrity, and so forth. However, it does not address the passing of intermediate products, which are still returned to the web application and must be trusted in that environment.

To mitigate risk of passing intermediate products, an entire computational network can be executed in the hosted computing framework. This approach, a superset of those described above, would involve specifying the computational network, loading all of the required modules, and then ordering an execution of the network within the trusted environment. This approach may also increase performance, as it avoids repeated roundtrips back to the web application made solely for the purpose of moving data from one processing stage to the other.

Embodiments of the present disclosure, for example, are described above with reference to block diagrams and/or operational illustrations of methods, systems, and computer program products according to embodiments of the present disclosure. The functions/acts noted in the blocks may occur out of the order as shown in any flowchart. For example, two blocks shown in succession may in fact be executed substantially concurrent or the blocks may sometimes be executed in the reverse order, depending upon the functionality/acts involved. Additionally, not all of the blocks shown in any flowchart need to be performed and/or executed. For example, if a given flowchart has five blocks containing functions/acts, it may be the case that only three of the five blocks are performed and/or executed. In this example, any of the three of the five blocks may be performed and/or executed.

The description and illustration of one or more embodiments provided in this application are not intended to limit or restrict the scope of the present disclosure as claimed in any way. The embodiments, examples, and details provided in this application are considered sufficient to convey possession and enable others to make and use the best mode of the claimed embodiments. The claimed embodiments should not be construed as being limited to any embodiment, example, or detail provided in this application. Regardless of whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the general inventive concept embodied in this application that do not depart from the broader scope of the claimed embodiments.

What is claimed is:

1. A method of securing genomic information, the method comprising:
receiving a genomic sequence from a source of genomic data;
generating a proxy patient identity for referencing the genomic sequence;

providing the genomic sequence to a managed computing pipeline, the computing pipeline being configured to process the genomic sequence so as to detect a feature in the genomic sequence;

annotating the detected feature, the detected feature and annotation together forming intermediate results;

storing the intermediate results in a data store;

obtaining the intermediate results from the managed computing pipeline at a hosted computing module comprising an isolated computing environment;

receiving, at an execution manager of the hosted computing module, a request to execute a user-specified program code configured to process the intermediate results to generate a set of informatics products;

decomposing, by the hosted computing module, the user-specified program code into individual computations within the isolated computing environment of the hosted computing module;

executing, by the hosted computing module, one or more requests from the user-specified program code for the stored intermediate results, wherein the stored intermediate results are provided to the isolated computing environment only if the user-specified program code is authorized to receive the stored intermediate results, performing each computation using the isolated computing environment of the hosted computing module;

auditing the results of the user-specified program code computations; and returning the results of the user-specified program code computations to a requester.

2. The method of claim 1, wherein the genomic sequence is received from a sequencing apparatus.

3. The method of claim 1 further comprising storing at least one of the detected feature, the annotated feature, and the proxy identity in a database according to an auditable sequence of execution of the hosted computing module.

4. The method of claim 1, wherein the hosted computing module is configured to annotate the detected feature according to a clinical relevance.

5. The method of claim 1, further comprising aligning the genomic sequence against a reference genomic sequence prior to providing the genomic sequence to the managed computing pipeline.

6. The method of claim 1, further comprising:
authenticating users using a security module of the hosted computing module; and
providing access control according to the user authentication.

7. The method of claim 1, wherein in the step of providing the genomic sequence to the managed computing pipeline, the managed computing pipeline is secured by one of user authentication, and role-based access control.

8. The method of claim 1, further comprising:
presenting at least one annotated feature and the associated patient proxy identity for clinical analysis.

9. An apparatus for providing genomic informatics, the apparatus comprising:
a receiver module configured to receive a genomic sequence from a source of genomic data;
a communication bus for providing the genomic sequence to a managed computing pipeline, the computing pipeline being configured to process the genomic sequence so as to detect a feature in the genomic sequence and annotate the detected feature, the detected feature and annotation together forming intermediate results, the intermediate results stored in a data store;
the communication bus being configured to obtain the intermediate results from the managed computing pipeline, and upon request to provide the intermediate results from the data store to a hosted computing module comprising an isolated computing environment; and the hosted computing module being configured to receive at an execution manager, a request to execute a user-specified program code configured to process the stored intermediate results to generate a set of informatics products, wherein the hosted computing module is further configured to: (1) decompose the user-specified program code into individual computations within the isolated computing environment of the hosted computing module, (2) execute one or more requests from the user-specified program code for stored intermediate results, wherein the stored intermediate results are provided to the isolated computing environment only if the user-specified program code is authorized to receive the stored intermediate results, (3) perform each computation using the isolated computing environment of the hosted computing module; (4) audit the results of the user-specified program code computations; and (5) return the results of the user-specified program code computations to a requester.

10. The apparatus of claim 9, wherein the source of genomic data is a sequencing apparatus.

11. The apparatus of claim 9 further comprising a non-transitory computer readable storage medium for storing at least one of the detected feature, the annotated feature, and the proxy identity in a database according to an auditable sequence of execution of the hosted computing module.

12. The apparatus of claim 9 wherein the hosted computing module is configured to annotate the detected feature according to a clinical relevance.

13. The apparatus of claim 9 further comprising a module configured to align the genomic sequence against a reference genomic sequence prior to providing the genomic sequence to the managed computing pipeline.

14. The apparatus of claim 9 wherein the hosted computing module comprises:
a program execution module comprising a virtualization container; and
a security module for authenticating users and providing access control according to the user authentication.

15. The apparatus of claim 9 wherein the managed computing pipeline is secured by one of user authentication and role-based access control.

16. The apparatus of claim 9 further comprising a user interface for presenting at least one annotated feature and the associated patient proxy identity for clinical analysis.

17. A method for performing a computation, the method comprising:
receiving a program for execution at a managed computing pipeline;
creating an execution context for the execution of the program;
launching a secure virtual machine within the execution context to execute the program;
receiving a genomic sequence and personally-identifiable information from a source of genomic data and annotating, by the program, a detected feature of the genome sequence to form intermediate results;
transmitting, upon request by the virtual machine, the intermediate results out of the managed computing pipeline to the virtual machine, wherein the intermediate results are provided to the virtual machine only if the program is authorized to receive the stored intermediate results;
executing the program within the virtual machine;
auditing the results of the executing program; and
returning the results of the executed program to a requester;
wherein the personally-identifiable information associated with the execution of the program is stored exclusively within the execution context.

18. The method of claim 17 further comprising creating an executable image from the uploaded program and saving the executable image to a non-transitory computer readable storage medium.

19. The method of claim 18 further comprising storing state information associated with the execution of the virtual machine in the non-transitory computer readable storage medium.

20. The method of claim 17 wherein the execution context is a virtualization container.

\* \* \* \* \*